US011442065B2

(12) United States Patent
Yang et al.

(10) Patent No.: US 11,442,065 B2
(45) Date of Patent: Sep. 13, 2022

(54) MARKER FOR GASTROINTESTINAL TUMORS

(71) Applicant: RHODE ISLAND HOSPITAL, Providence, RI (US)

(72) Inventors: Wentian Yang, Pawtucket, RI (US); Lijun Wang, Providence, RI (US); Douglas C. Moore, Barrington, RI (US)

(73) Assignee: Rhode Island Hospital, Providence, RI (US)

( * ) Notice: Subject to any disclaimer, the term of this patent is extended or adjusted under 35 U.S.C. 154(b) by 181 days.

(21) Appl. No.: 16/834,981

(22) Filed: Mar. 30, 2020

(65) Prior Publication Data

US 2020/0378974 A1 Dec. 3, 2020

Related U.S. Application Data

(60) Provisional application No. 62/854,600, filed on May 30, 2019.

(51) Int. Cl.
*G01N 33/574* (2006.01)
*A61K 45/06* (2006.01)

(52) U.S. Cl.
CPC .. *G01N 33/57446* (2013.01); *G01N 33/57484* (2013.01); *A61K 45/06* (2013.01)

(58) Field of Classification Search
CPC ....... G01N 33/57484; G01N 33/57446; A61K 45/06
See application file for complete search history.

(56) References Cited

U.S. PATENT DOCUMENTS 7,160,722 B2 1/2007 De

FOREIGN PATENT DOCUMENTS

WO 3244380 A2 6/2002

OTHER PUBLICATIONS

Qu et al, Osterix promotes the migration and angiogenesis of breast cancer by upregulation of S100A4 expression, J Cell Mol Med, 2019, 23, pp. 1116-1127 (Year: 2019).*
Barker, et al., "Identification of Stem Cells in Small Intestine and Colon by Marker Gene Lgr5", Nature, vol. 449, Oct. 25, 2007, pp. 1003-1007.
Barker, et al., "Identifying the Stem Cell of the Intestinal Crypt: Strategies and Pitfalls", Cell Stem Cell, vol. 11, Oct. 5, 2012, pp. 452-460.
Bi, et al., "Sox9 is Required for Cartilage Formation", Nature Genetics, vol. 22, Issue 1, May 1999, pp. 85-89.
Clevers, et al., "Snapshot: The Intestinal Crypt", Cell, vol. 152, 2013, pp. 1198-1198.e2.
Clevers, "The Intestinal Crypt, A Prototype Stem Cell Compartment", Cell, vol. 154, Jul. 18, 2013, pp. 274-284.
Coulombe, et al., "Epithelial Tyrosine Phosphatase SHP-2 Protects against Intestinal Inflammation in Mice", Molecular and Cellular Biology, vol. 33, No. 11, Jun. 2013, pp. 2275-2284.
Coulombe, et al., "SHP-2 Phosphatase Prevents Colonic Inflammation by Controlling Secretory Cell Differentiation and Maintaining Host-Microbiota Homeostasis", Journal of Cellular Physiology, vol. 231, 2016, pp. 2529-2540.
Dai, et al., "Osterix Transcriptional Factor is Involved in the Metastasis of Human Breast Cancers", Oncology Letters, vol. 10, 2015, pp. 1870-1874.
Engin, et al., "Modulation of Anxiety and Fear via Distinct Intrahippocampal Circuits", eLife, vol. 5, Issue e14120, 2016, pp. 1-23.
Engin, et al., "Notch Signaling Contributes to the Pathogenesis of Human Osteosarcomas", Human Molecular Genetics, vol. 18, No. 8, 2009, pp. 1464-1470.
Fan, et al., "Murine Colonic Organoid Culture System and Downstream Assay Applications", Methods in Molecular Biology, vol. 1576, 2016, pp. 171-181.
Feil, et al., "Ligand-activated Site-specific Recombination in Mice", Proceedings of the National Academy of Sciences, vol. 93, Oct. 1996, pp. 10887-10890.
Flier, et al., "OLFM4 Is a Robust Marker for Stem Cells in Human Intestine and Marks a Subset of Colorectal Cancer Cells", Gastroenterology, vol. 137, Issue 1, Jul. 2009, pp. 15-17.
Gagné-Sansfacon, et al., "The Tyrosine Phosphatase Shp-2 Confers Resistance to Colonic Inflammation by Driving Goblet Cell Function and Crypt Regeneration", Journal of Pathology, vol. 247, 2019, pp. 135-146.
Ghatalia, et al., "Clinical Utilization Pattern of Liquid Biopsies (LB) to Detect Actionable Driver Mutations, Guide Treatment Decisions and Monitor Disease Burden During Treatment of 33 Metastatic Colorectal Cancer (mCRC) Patients (pts) at a Fox Chase Cancer Center Gl Oncology Subspecialty Clinic", Frontiers in Oncology, vol. 8, Article 652, Jan. 17, 2019, pp. 1-8.
Haraldsdottir, et al., "Integrating Anti-EGFR Therapies in Metastatic Colorectal Cancer", Journal of Gastrointestinal Oncology, vol. 4, No. 3, 2013, pp. 285-298.
He, et al., "BMP Signaling Inhibits Intestinal Stem Cell Self-Renewal Through Suppression of Wnt-β-Catenin Signaling", Nature Genetics, vol. 36, No. 10, Oct. 2004, pp. 1117-1121.
Heuberger, et al., "Shp2/MAPK Signaling Controls Goblet/Paneth Cell Fate Decisions in the Intestine", Proceedings of the National Academy of Sciences, vol. 111, No. 9, Mar. 4, 2014, pp. 3472-3477.
Jourdan, et al., "Tissue Microarray Technology: Validation in Colorectal Carcinoma and Analysis of P53, hMLH1, and hMSH2 Immunohistochemical Expression", Virchows Archiv, vol. 443, 2013, pp. 115-121.
Kawakami, et al., "587P—The Impact of Late-Line Treatment on Overall Survival (OS) From the Initiation of First-Line Chemotherapy (CT) for Patients (pts) With Metastatic Colorectal Cancer (mCRC)", Annals of Oncology, vol. 30, Supplement 5, Oct. 2019, pp. v222.

(Continued)

*Primary Examiner* — Misook Yu
*Assistant Examiner* — Dennis J Sullivan
(74) *Attorney, Agent, or Firm* — Adler Pollock & Sheehan P.C.

(57) ABSTRACT

The invention provides that OSTERIX (a.k.a. SP7) is a marker for gastrointestinal stem cells and that OSTERIX is expressed widely and at elevated levels in human gastrointestinal tumors.

5 Claims, 4 Drawing Sheets

(56) References Cited

OTHER PUBLICATIONS

Kosinski, et al., "Gene Expression Patterns of Human Colon Tops and Basal Crypts and BMP Antagonists as ntestinal Stem Cell Niche Factors", PNAS, vol. 104, No. 39, Sep. 25, 2007, pp. 15418-15423.
Lamba, et al., "Current Management and Prognostic Features for Gastrointestinal Stromal Tumor (GIST)", Experimental Hematology & Oncology, vol. 1, No. 14, 2012, pp. 1-10.
Madisen, et al., "A Robust and High-throughput Cre Reporting and Characterization System for the Whole Mouse Brain", Nature Neuroscience, vol. 13, Issue 1, Jan. 2010, pp. 133-140.
Maes, et al., "Osteoblast Precursors, but Not Mature Osteoblasts, Move into Developing and Fractured Bones along with Invading Blood Vessels", Developmental Cell, vol. 19, No. 2, Aug. 17, 2010, pp. 329-344.
Maron, et al., "Targeted Therapies for Targeted Populations: Anti-EGFR Treatment for EGFR-Amplified Gastroesophageal Adenocarcinoma", Cancer Discovery, vol. 8, No. 6, Jun. 2018, pp. 696-713.
Meran, et al., "Intestinal Stem Cell Niche: The Extracellular Matrix and Cellular Components", Stem Cells International, vol. 2017, Article ID 7970385, Aug. 1, 2017, 11 pages.
Mizoguchi, et al., "Osterix Marks Distinct Waves of Primitive and Definitive Stromal Progenitors During Bone Marrow Development", Developmental Cell, vol. 29, Issue 3, May 12, 2014, pp. 340-349.
Nakamura, et al., "HER2-Targeted Therapy Should Be Shifted Towards an Earlier Line for Patients With Anti-EGFR-Therapy Naïve, HER2-Amplified Metastatic Colorectal Cancer", ESMO Open,vol. 4, e000530, 2019, pp. 1-2.
Nakashima, et al., "The Novel Zinc Finger-Containing Transcription Factor Osterix Is Required for Osteoblast Differentiation and Bone Formation", Cell, vol. 108, Jan. 11, 2002, pp. 17-29.
Neel, et al., "SH2-Domain-Containing Protein-Tyrosine Phosphatases", Handbook of Cell Signaling (Second Edition), Dec. 2010, pp. 771-809.
O'Rourke, et al., "Isolation, Culture, and Maintenance of Mouse Intestinal Stem Cells", Bio Protocol, vol. 6, Issue 4, Feb. 20, 2016, pp. 1-15.
Pirvulet, "Gastrointestinal Stem Cell Up-to-Date", Journal of Medicine and Life, vol. 8, Issue 2, Apr.-Jun. 2015, pp. 245-249.
Qi, et al., "BMP Restricts Sternness of Intestinal Lgr5+ Stem Cells by Directly Suppressing Their Signature Genes", Nature Communications, vol. 8, Article 13824, Jan. 6, 2017, pp. 1-14.
Qu, et al., "Osterix Promotes the Migration and Angiogenesis of Breast Cancer by Upregulation of S100A4 Expression", Journal of Cellular and Molecular Medicine, vol. 23, 2019, pp. 1116-1127.
Roche, et al., "SOX9 Maintains Reserve Stem Cells and Preserves Radioresistance in Mouse Small Intestine", Gastroenterology, vol. 149, Issue 6, Nov. 2015, pp. 1553-1563.e10.
Rodda, et al., "Distinct Roles for Hedgehog and Canonical Wnt Signaling in Specification, Differentiation and Maintenance of Osteoblast Progenitors", Development, vol. 133, 2006, pp. 3231-3244.
Salazar, et al., "BMP Signalling in Skeletal Development, Disease and Repair", Nature Reviews Endocrinology, vol. 12, No. 4, Feb. 2016, pp. 1-19.
Sato, et al., "Paneth Cells Constitute the Niche for Lgr5 Stem Cells in Intestinal Crypts", Nature, vol. 469, No. 7330, Jan. 20, 2011, pp. 415-418.
Sato, et al., "Single Lgr5 Stem Cells Build Crypt-Villus Structures in Vitro Without a Mesenchymal Niche", Nature, vol. 459, May 14, 2009, pp. 262-265.
Ulsamer, et al., "BMP-2 Induces Osterix Expression through Up-regulation of Dlx5 and Its Phosphorylation by p38", The Journal of Biological Chemistry vol. 283, No. 7, Feb. 15, 2008, pp. 3816-3826.
Yamashita, et al., "Role of the Protein Tyrosine Phosphatase Shp2 in Homeostasis of the Intestinal Epithelium", Plos One, vol. 9, Issue 3, Mar. 2014, 11 pages.
Yang, et al., "An Shp2/SFK/Ras/Erk Signaling Pathway Controls Trophoblast Stem Cell Survival", Developmental Cell, vol. 10, Mar. 2006, pp. 317-327.
Yang, et al., "Clinicopathological Characteristics and Prognostic Factors of Gastrointestinal Stromal Tumors in Chinese Patients", Oncology Letters, vol. 16, 2018, pp. 4905-4914.
Yang, et al., "Ptpn11 Deletion in A Novel Cartilage Cell Causes Metachondromatosis by Activating Hedgehog Signaling", Nature, vol. 499, Issue 7459, Jul. 25, 2013, pp. 491-495.
Zuo, et al., "SHP2 Regulates Skeletal Cell Fate by Modifying Sox9 Expression and Transcriptional Activity", Bone Research, vol. 6, Issue 12, Apr. 6, 2018, 13 pages.

\* cited by examiner

4(A)

| Tg(Sp7-tTA,tetO-GFP/Cre;Ptpn11^(fl/+)) | SHP2_Sp7 CTR |
| Tg(Sp7-tTA,tetO-GFP/Cre;Ptpn11^(fl/fl)) | SHP2_Sp7 KO |
| Tg(CMV-CreER;Ptpn11^(fl/+)) | SHP2_Cmv CTR/ER |
| Tg(CMV-CreER;Ptpn11^(fl/fl)) | SHP2_Cmv KO/ER |
| Tg(Bglap-Cre;Ptpn11^(fl/+)) | SHP2_Bglap CTR |
| Tg(Bglap-Cre;Ptpn11^(fl/fl)) | SHP2_Bglap KO |

4(B)

4(C)

MARKER FOR GASTROINTESTINAL TUMORS

REFERENCE TO RELATED APPLICATIONS

This patent application claims priority to provisional patent application U.S. Ser. No. 62/854,600, entitled "Marker for gastrointestinal stem cells and tumors."

STATEMENT REGARDING FEDERALLY SPONSORED RESEARCH OR DEVELOPMENT

This invention was made with government support under R01 AR066746 awarded by the National Institutes of Health. The government has certain rights in the invention.

FIELD OF THE INVENTION

This invention generally relates to expression markers, specifically defined cancers of the colon, and specifically defined cancers of the stomach and intestines.

BACKGROUND OF THE INVENTION

Gastrointestinal (GI) diseases, particularly gastrointestinal tumors, are costly and clinically burdensome. The location of origin classifies gastrointestinal tumors, for example, colorectal carcinoma (CRC), gastric carcinoma, gastro-oesophageal junction (GOJ) adenocarcinomas, and gastrointestinal stromal tumors (GISTs), etc. Colorectal carcinomas are the most common. Colorectal carcinoma is routinely surveilled for by colonoscopy. Several biomarkers have been used in colorectal carcinoma diagnosis, prognosis, and treatment, including carcinoembryonic antigen (CEA) and cancer-related antigen 19-9 (CA19-9). More recently, patients with a specific mutation in K-ras can be diagnosed by a K-ras mutation antibody. These patients benefit from anti-EGFR therapy.

OSTERIX had been considered by the biomedical art to be an osteoblast-specific transcription factor. Nakashima et al., Cell, 108, 17-29 (2002); Mizoguchi et al., Dev. Cell., 29, 340-349 (2014). OSTERIX is not expressed beyond the mesengenic lineages of bone and cartilage, except in some cancers. Engin et al., Hum. Mol. Genet., 18, 1464-1470 (2009); Dai et al., Oncol. Lett., 10, 1870-1874 (2015); and Qu et al., J. Cell. Mol. Med., 23, 1116-1127 (2019). Previously, to generate SHP2 floxed allele and Sp-Cre mice, the inventors crossed Tg(Sp7-Cre) with $Ptpn11^{fl/+}$ mice to explore the role of SHP2 in OSTERIX-expressing preosteoblasts. The $SHP2_{Sp7}KO$ mice developed fatal gastrointestinal (GI) pathology, with dramatic villus hypoplasia. Rodda & McMahon, Development, 133, 3231-3244 (2006); and Yang et al., Dev. Cell., 10, 317-327 (2006).

There is a need in the biomedical and oncological arts for other markers of gastrointestinal tumors. Defining markers useful for early, specific, and differential diagnosis and treatment of gastrointestinal tumors would have a beneficial impact on the therapy and prognosis of gastrointestinal tumors.

SUMMARY OF THE INVENTION

The invention provides that OSTERIX (aka SP7) is a marker for gastrointestinal stem cells and that OSTERIX is expressed widely and at elevated levels in human gastrointestinal tumors. The invention is useful for the diagnosis of gastrointestinal (GI) and other tissue tumors, the prognosis of patients with gastrointestinal tumors, and the treatment of these patients.

In one aspect of the invention, OSTERIX is expressed in crypt base stem cells, and that SHP2 expression in these cells is critical for self-renewal and proliferation. The inventors found a strong expression of Rosa26ZSG:Sp7-Cre reporter in the crypts and villi of $SHP2_{Sp7}CTR$ mice. Subsequent immunostaining revealed OSTERIX expression at the crypt base, coocalized with OLFM4, a bona fide gastrointestinal stem cell marker.

In the first embodiment, the invention provides for the use of an anticancer agent in the treatment of gastrointestinal cancer in a patient. The treatment comprises the steps of (a) assaying a biological sample from the patient, (b) determining if a patient has an increased level of OSTERIX marker as compared to a biological sample from a patient without gastrointestinal cancer, and, if an increased level of OSTERIX marker is present, then (c) administering a therapeutically effective amount of the anticancer agent to the patient.

In a second embodiment, the invention provides for the use of an OSTERIX marker in the assessment of gastrointestinal cancer. An increased amount of an OSTERIX marker in a biological sample from a subject as compared to normal healthy controls indicates gastrointestinal cancer.

In a third embodiment, the invention provides for the use of an antibody directed against OSTERIX protein in the assessment of gastrointestinal cancer. An increased concentration of OSTERIX protein in a gastrointestinal sample from a subject as compared to normal healthy controls indicates gastrointestinal cancer.

In a fourth embodiment, the invention provides a method for selectively treating gastrointestinal cancer in a patient in need thereof. The method comprises the steps of (a) selecting a patient for treatment with an anticancer agent based on the patient having an increased level of OSTERIX marker as compared to a patient without gastrointestinal cancer, and (b) administering an anticancer agent to the patient.

In a fifth embodiment, the invention provides a method for diagnosing gastrointestinal cancer in a subject. The method comprises the steps of (a) providing a biological sample from the subject; (b) determining the amount in the sample of an OSTERIX marker; and (b) comparing the amount of an OSTERIX marker in the biological sample to a control amount of an OSTERIX marker in a corresponding sample, wherein the subject is diagnosed as having gastrointestinal cancer if there is a measurable increase in the amount of an OSTERIX marker in the subject's biological sample as compared to the amount of an OSTERIX marker in the control biological sample.

In a sixth embodiment, the invention provides a method for determining whether to initiate or continue prophylaxis or treatment of gastrointestinal cancer in a subject. The method comprises the steps of (a) providing a series of biological samples from the subject over a time period; (b) analyzing the series of biological samples to determine the amount of an OSTERIX marker in the subject's biological sample; (c) determining the measurable change in the amount of an OSTERIX marker in the biological samples to decide whether to initiate or continue the prophylaxis or therapy of gastrointestinal cancer.

In a seventh embodiment, the invention provides a method for identifying gastrointestinal stem cells in a gastrointestinal sample. The method comprises the steps of (a) providing a gastrointestinal sample; (b) analyzing the gastrointestinal sample to determine the amount of an OSTERIX marker; (c) identifying gastrointestinal stem cells in a gastrointestinal sample by the expression of an OSTERIX marker in the cells in the gastrointestinal sample. The co-localization studies provided in this specification show that OSTERIX is a marker of gut stem cells.

As shown in the EXAMPLES below, the inventors' studies of SHP2's function in osteoblast biology led to the discovery of OSTERIX expression in gastrointestinal crypt stem cells and progenitors, and of the regulatory role of SHP2 in Osterix crypt cells influencing stem cell self-renewal, proliferation, and epithelium development. The colocalization of OSTERIX with OLFM4 in the crypt cells shows that OSTERIX is a novel marker for stem cells. OSTERIX significantly associates with colonic adenocarcinoma, showing that OSTERIX is a marker for tumor diagnosis.

DETAILED DESCRIPTION OF THE INVENTION

Industrial Applicability

Figure 1:
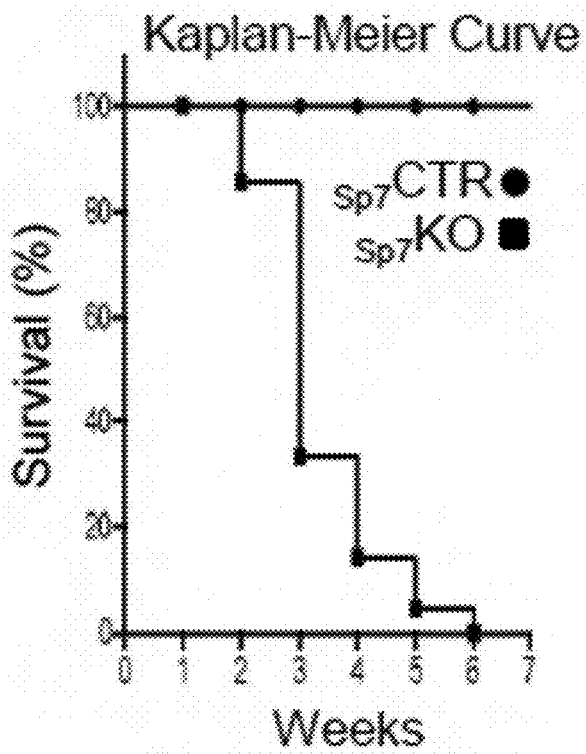
FIG. 1 is a pair of Kaplan-Meier survival curves of $SHP2_{Sp7}$CTR and $SHP2_{Sp7}$KO mice, showing >70% mortality at four weeks in $SHP2_{Sp7}$KO mice, and 100% mortality by six weeks in $SHP2_{Sp7}$KO mice. $x2$ test, *$p<0.05$ (n=21, per genotype).

The findings in this specification provide a foundation for new avenues of inquiry into intestinal stem cell regulation and biology. Gastrointestinal OSTERIX expression assays and treatment may have therapeutic potential because, as demonstrated in this specification, OSTERIX is expressed in malignancies. The invention is valuable for the diagnosis of gastrointestinal and other tissue tumors, including but not limited to, colorectal carcinoma, adenocarcinomas, and gastrointestinal stromal tumors. The invention is also informative to the prognosis of patients with gastrointestinal tumors, evaluation of anti-tumor efficacy, and study of gastrointestinal stem cell biology. Clinicians, particularly oncologists and pathologists, and basic scientists, would be the primary user of this invention.

Definitions

For convenience, the meaning of some terms and phrases used in the specification, examples, and appended claims, are provided below. Unless stated otherwise or implicit from context, these words and phrases have the meanings provided below. These definitions are provided to aid in describing particular embodiments and are not intended to limit the claimed invention. Unless otherwise defined, all technical and scientific terms have the same meaning as commonly understood by one of ordinary skill in the biomedical art. If there is an apparent discrepancy between the usage of a word in the biomedical art and its definition provided in this specification, the definition provided in this specification shall prevail.

"Antibodies" means immunoglobulin molecules and immunologically active portions of immunoglobulin (Ig) molecules, i.e., molecules that contain an antigen-binding site that binds specifically (i.e., immunoreacts with) an antigen. These include, but are not limited to, polyclonal, monoclonal, chimeric, single chain, Fc, Fab, Fab', and Fab2 fragments, and a Fab expression library. Antibody molecules relate to the classes IgG, IgM, IgA, IgE, and lgD, which differ from one another by heavy chain present in the molecule. These include subclasses, such as IgG1, IgG2, and others. The light chain may be a kappa chain or a lambda chain. Also included are chimeric antibodies, for example, monoclonal antibodies or fragments thereof that are specific to more than one source, e.g., a mouse or human sequence. Further included are camelid antibodies, shark antibodies, or nanobodies. Data in this specification was generated using commercially-available antibodies.

"Anticancer agent" means agents or drugs used against or arresting or prevent cancer. See, Merriam-Webster Dictionary, online, https://www.merriam-webster.com/dictionary/anticancer.

"Bglap" (Osteocalcin, bone gamma-carboxyglutamic acid-containing protein) is a small noncollagenous protein hormone found in bone and dentin, first identified as a calcium-binding protein in chick bone.

"Biological sample" is a biological specimen, including blood, tissue, urine, etc. taken from a participant. OECD, 2006; Creation and Governance of Human Genetic Research Databases, OECD. Paris. Science and technology statistics, Monday, Jul. 23, 2007. A biological sample of gastrointestinal tissue is a "gastrointestinal sample."

"Cancer" means the physiological condition in mammals typically characterized by abnormal or unregulated cell growth. Specifically included are gastrointestinal cancers, such as the esophageal, stomach, small bowel, large bowel, anal, and rectal cancers, including are gastric and colorectal cancers.

"Classification Rate" is the proportion of all samples correctly classified by the prediction model (be that as positive or negative).

"Diagnosis" means the identification of an illness or other problem.

"Differentially expressed gene," "differential gene expression," and like phrases, refer to a gene whose expression is activated to a higher or lower level in a subject (e.g., test sample), specifically cancer, such as gastrointestinal cancer, relative to its expression in a control subject (e.g., control sample). The terms also include genes whose expression is activated to a higher or lower level at different stages of the same disease, in recurrent or non-recurrent illness, or cells with higher or lower levels of proliferation. A differentially expressed gene may be activated or inhibited at the polynucleotide level or polypeptide level or may be subject to alternative splicing to result in a different polypeptide product.

"Marker" or "biomarker" means a molecule associated quantitatively or qualitatively with the presence of a biological phenomenon. A marker can be a polynucleotide, such as a gene or a gene fragment, RNA or RNA fragment, or a polypeptide such as a peptide, oligopeptide, protein, or protein fragment; or any related metabolites, by-products, or any other identifying molecules, such as antibodies or antibody fragments, whether related directly or indirectly to a mechanism underlying the phenomenon. In this specification, the markers are OSTERIX protein, Osx gene or gene expression product, and variants thereof.

"Normal control" as used in this specification means either a control value known in the oncological art for patients without gastrointestinal cancer or a control value that has determined by a measurement taken from a subject without gastrointestinal cancer as compared with a measurement taken from the subject being tested. These normal healthy control values are expected to be very similar. If a conflict occurs, the control value known in the oncological art for patients without gastrointestinal cancer will be taken as the correct normal healthy control value.

"OLFM4" (Olfactomedin 4) is an antiapoptotic factor that promotes tumor growth and is an extracellular matrix glycoprotein that facilitates cell adhesion. See van der Flier et al., Gastroenterology, 137, 15-17 (2009).

"OSTERIX" (OSX, SP7) is a protein that in humans is encoded by the Sp7 gene. OSTERIX has traditionally been considered in the biomedical art as a bone cell-specific transcription factor (typically characterized as comprising a zinc finger domain and a transactivation domain comprising a proline-rich domain), principally associated with the osteoblastic differentiation of mesenchymal stem cells. Nakashima et al., Cell, 108, 17-29 (2002); and Mizoguchi et al., Dev. Cell., 29, 340-349 (2014). OSTERIX is a master regulator of bone because OSTERIX controls the differentiation of pre-osteoblasts into mature and functional osteoblasts. OSX-null mice form few osteoblasts and lack intramembranous or endochondral bone. See, U.S. Pat. No. 7,160,722 (de Crombrugghe et al.), "Master bone formation transcription factor: compositions and methods of use." OSTERIX is not expressed beyond the mesengenic lineages of bone and cartilage, except in certain cancers. Engin et al., Hum. Mol. Genet., 18, 1464-1470 (2009); Dai at al., Oncol. Lett., 10, 1870-1874 (2015); and Qu et al., J. Cell. Mol. Med., 23, 1116-1127 (2019).

"Prognosis" is the prediction of medical outcomes (e.g., likelihood of long-term survival). A negative prognosis, or adverse outcome, includes a projection of relapse, disease progression (e.g., tumor growth or metastasis, or drug resistance), or mortality. A positive prognosis, or favorable outcome, includes a prediction of disease remission (e.g., disease-free status), amelioration (e.g., tumor regression), or stabilization.

"Proliferation," as used in this specification, has the biological art meaning of cell processes leading to increased cell size or cell number. It can include one or more of: tumor or cell growth, angiogenesis, innervation, and metastasis.

"Sensitivity" has the biological art meaning of the proportion of positive samples also predicted to be positive. In a test for cancer recurrence, sensitivity is the proportion of recurrent tumors predicted to recur.

"SHP2" (Src homology region 2 domain-containing phosphatase-2) is a member of the protein tyrosine phosphatase (PTP) family. PTPs are known to be signaling molecules that regulate a variety of cellular processes, including cell growth, differentiation, mitotic cycle, and oncogenic transformation. Protein tyrosine phosphatase non-receptor type 11 (PTPN11) encodes the tyrosine phosphatase SHP-2 that is overexpressed in gastric cancer.

"Specificity" or "selectivity" has the biological art meaning of the proportion of negative samples also predicted to be negative. In a test for cancer recurrence, specificity equates to the proportion of non-recurrent samples predicted to by non-recurrent by the model.

"Therapeutically effective" means the amount sufficient to treat disease or disorders by remedial agents or methods, producing a useful or favorable result or effect. See, Merriam-Webster Dictionary, online, https://www.merriam-webster.com/dictionary/therapeutic.

"Treat," "treatment," treating," or "amelioration," when used referring to a disease, disorder or medical condition, means the therapeutic treatment for a condition, The object is to reverse, alleviate, ameliorate, inhibit, slow down or stop the progression or severity of a symptom or condition. The term treating includes reducing or alleviating at least one adverse effect or symptom of a condition. The term treating does not require that the disorder, condition, or associated symptoms be eliminated entirely.

"Tumor" means cells with neoplastic cell growth and proliferation, whether malignant or benign and all pre-cancerous and cancerous cells and tissues.

Enabling References

Those having ordinary skill in the biomedical art can use one or more of these patents and publications as guidance to predictable results when making and using the invention.

WO 2002/044380 A2 (University of Texas System), "Master bone" "formation transcription factor compositions and methods of use." A novel gene expressed selectively by osteoblast lines is provided. Expression of the gene is highly restricted to cells of osteoblast lineage, including precursor cells. Also provided is a method for promoting bone formation by providing agents that bind to the novel gene within osteoblast cells to stimulate bone formation.

Barker et al., "Identification of stem cells in small intestine and colon by marker gene Lgr5." Nature, 449, 1003-1007 (2007). The cells at the base of the intestinal crypts are intestinal stem cells and Paneth cells, with an occasional label-retaining cell.

Barker et al., "Identifying the stem cell of the intestinal crypt: strategies and pitfalls." Cell Stem Cell, 11, 452-460 (2012). The cells at the base of the intestinal crypts are intestinal stem cells and Paneth cells, with an occasional label-retaining cell.

Bi et al., "Sox9 is required for cartilage formation." Nature Genetics, 22, 85-89 (1999). OSTERIX may be a significant factor in gut homeostasis, analogous to SOX9's dual role as a master regulator of cartilage formation.

Clevers & Batlle, "SnapShot: the intestinal crypt." Cell, 152, 1198-1198 e1192 (2013). The cells at the base of the intestinal crypts are intestinal stem cells and Paneth cells, with an occasional label-retaining cell.

Clevers, "The intestinal crypt, a prototype stem cell compartment." Cell, 154, 274-284 (2013). The cells at the base of the intestinal crypts are intestinal stem cells and Paneth cells, with an occasional label-retaining cell.

Coulombe et al., "Epithelial tyrosine phosphatase SHP-2 protects against intestinal inflammation in mice." Mol. Cell. Biol. 33, 2275-2284 (2013). This publication shows how SHP2 is involved in intestinal crypt cell differentiation and epithelial homeostasis.

Coulombe et al., "SHP-2 Phosphatase Prevents Colonic Inflammation by Controlling Secretory Cell Differentiation and Maintaining Host-Microbiota Homeostasis." J. Cell Physiol., 231, 2529-2540 (2016). This publication shows how SHP2 is involved in intestinal crypt cell differentiation and epithelial homeostasis. SHP2 was reported to reduce goblet and Paneth cell numbers in a villin-Cre mouse model.

Dai et al., "Osterx transcriptional factor is involved in the metastasis of human breast cancers." Oncol. Lett., 10, 1870-1874 (2015). OSTERIX is not expressed beyond the mesengenic lineages of bone and cartilage, except in certain cancers.

Engin et al., "Notch signaling contributes to the pathogenesis of human osteosarcomas." Hum. Mol. Genet., 18, 1464-1470 (2009). OSTERIX is not expressed beyond the mesengenic lineages of bone and cartilage, except in certain cancers.

Fan et al., "Murne colonic organoid culture system and downstream assay applications." Methods Mol. Biol. (2016). This publication shows how to create crypt organoid cultures.

Feil et al., "Ligand-activated site-specific recombination in mice." Proc. Natl. Acad. Sci. U.S.A., 93, 10887-10890 (1996).

Gagne-Sansfacon et al., "The tyrosine phosphatase Shp-2 confers resistance to colonic inflammation by driving goblet cell function and crypt regeneration." J. Pathol., 247, 135-146 (2019). This publication shows how SHP2 is involved in intestinal crypt cell differentiation and epithelial homeostasis.

He et al., "BMP signaling inhibits intestinal stem cell self-renewal through suppression of Wnt-beta-catenin signaling." Nature Genetics, 36, 1117-1121 (2004). BMP4 is expressed by mesenchymal cells adjacent to the crypt, where it downregulates the self-renewal and proliferation of the crypt stem cells.

Heuberger et al., "Shp2/MAPK signaling controls goblet/Paneth cell fate decisions in the intestine." Proc. Natl. Acad. Sci. U.S.A., 111, 3472-3477 (2014). This publication shows how SHP2 is involved in intestinal crypt cell differentiation and epithelial homeostasis. SHP2 was reported to reduce goblet and Paneth cell numbers in a villin-Cre mouse model.

Jourdan et al., "Tissue microarray technology: validation in colorectal carcinoma and analysis of p53, hMLH1, and hMSH2 immunohistochemical expression." Virchows Arch., 443, 115-121 (2003).

Kosinski et al., "Gene expression patterns of human colon tops and basal crypts and BMP antagonists as intestinal stem cell niche factors," Proc. Natl. Acad. Sci. USA., 104(39): 15418-15423 (Sep. 25, 2007), applied gene expression analysis of healthy human colon tops and basal crypts by using expression microarrays with 30,000 genes. Nine hundred and sixty-nine cDNA clones were found to be differentially expressed between human colon crypts and tops. Pathway analysis revealed the differential expression of genes involved in cell cycle maintenance and apoptosis, as well as genes in bone morphogenetic protein (BMP), Notch, Wnt, EPH, and MYC signaling pathways. BMP antagonists gremlin 1, gremlin 2, and chordin-like 1 were found to be expressed by colon crypts. In situ hybridization and RT-PCR confirmed that these BMP antagonists are expressed by intestinal cryptal myofibroblasts and smooth muscle cells at the colon crypt. In vitro analysis demonstrated that gremlin 1 partially inhibits Caco-2 cell differentiation upon confluence and activates Wnt signaling in healthy rat intestinal epithelial cells. Collectively, the expression data set provides a comprehensive picture of human colonic epithelial cell differentiation.

Madisen et al., "A robust and high-throughput Cre reporting and characterization system for the whole mouse brain." Nature Neuroscience, 13, 133-140 (2010).

Maes et al., "Osteoblast precursors, but not mature osteoblasts, move into developing and fractured bones along with invading blood vessels." Dev. Cell 19, 329-344 (2010). Cre activity was made inducible by tamoxifen, and its expression was driven by the chicken beta-actin promoter/enhancer coupled with the cytomegalovirus (CMV) immediate-earty enhancer (Cmv-CreER).

Mizoguchi et al., "Osterix marks distinct waves of primitive and definitive stromal progenitors during bone marrow development." Dev. Cell., 29, 340-349 (2014). OSTERIX is considered to be an osteoblast-specific transcription factor.

Nakashima et al., "The novel zinc finger-containing transcription factor osterix is required for osteoblast differentiation and bone formation." Cell, 108, 17-29 (2002). OSTERIX is considered to be an osteoblast-specific transcription factor.

Neel et al., "SH2 Domain-Containing Protein-Tyrosine Phosphatases." Handbook of Cell Signaling, 771-809 (2009). The ubiquitously expressed Src homology 2-containing protein tyrosine phosphatase SHP2, encoded by PTPN11, is crucial for the development and/or maintenance of multiple tissues and organs.

O'Rourke et al., "Isolation, Culture, and Maintenance of Mouse Intestinal Stem Cells." Bio. Protoc., 6 (2016).

Pirvulet, "Gastrointestinal stem cell up-to-date." J. Med. Life, 8(2): 245-249 (April-June 2015). A general review of gastrointestinal stem cells is provided.

Qi et al., "BMP restricts stemness of intestinal Lgr5(+) stem cells by directly suppressing their signature genes." Nature Communications, 8, 13824 (2017). BMP4 is expressed by mesenchymal cells adjacent to the crypt, where it downregulates the self-renewal and proliferation of the crypt stem cells.

Qu at al., "Osterix promotes the migration and angiogenesis of breast cancer by upregulation of S100A4 expression." J. Cell. Mol. Med., 23, 1116-1127 (2019). OSTERIX is not expressed beyond the mesengenic lineages of bone and cartilage, except in some cancers.

Roche et al., "SOX9 maintains reserve stem cells and preserves radioresistance in mouse small intestine." Gastroenterology, 149, 1553-1563 e1510 (2015). OSTERIX may be an important regulator of crypt reserve cell biology.

Rodda & McMahon, "Distinct roles for Hedgehog and canonical Wnt signaling in specification, differentiation and maintenance of osteoblast progenitors." Development, 133, 3231-3244 (2006). The inventors previously crossed Tg(Sp7-Cre) with Ptpn11$^{fl/+}$ mice to explore the role of SHP2 in OSTERIX-expressing preosteoblasts. The SHP2$_{Sp7}$KO mice developed fatal gastrointestinal (GI) pathology, with dramatic villus hypoplasia.

Salazar et al., "BMP signaling in skeletal development, disease and repair." Nat. Rev. Endocrinol. 12, 203-221 (2016). Bone morphogenetic proteins (BMPs) induce and osteogenic differentiation of skeletal progenitors.

Sato at al. "Paneth cells constitute the niche for Lgr5 stem cells in intestinal crypts". Nature, 469, 415-418 (2011).

Sato et al., "Single Lgr5 stem cells build crypt-villus structures in vitro without a mesenchymal niche." Nature, 459, 262-265 (2009). This publication shows how to create crypt organoid cultures.

Ulsamer et al., "BMP-2 induces Osterix expression through up-regulation of Dlx5 and its phosphorylation by p38." J. Biol. Chem., 283, 3816-3826 (2008). Bone morphogenetic proteins (BMPs) induce Osterix expression.

van der Flier et al., "OLFM4 is a robust marker for stem cells in human intestine and marks a subset of colorectal cancer cells." Gastroenterology, 137, 15-17 (2009).

Yamashita et al., "Role of the protein tyrosine phosphatase Shp2 in homeostasis of the intestinal epithelium." PloS one 9, e92904 (2014). SHP2 was reported to reduce goblet and Paneth cell numbers in a villin-Cre mouse model Yang et al., "An Shp2/SFK/Ras/Erk signaling pathway controls trophoblast stem cell survival." Dev. Cell., 10, 317-327 (2006). The inventors previously crossed Tg(Sp7-Cre)8 with Ptpn11$^{fl/+}$ mice to explore the role of SHP2 in OSTERIX-expressing preosteoblasts. The SHP2$_{Sp7}$KO mice developed fatal gastrointestinal (GI) pathology, with dramatic villus hypoplasia.

Yang et al., "Ptpn11 deletion in a novel progenitor causes metachondromatosis by inducing hedgehog signalling." Nature, 499, 491-495 (2013). The inventors previously elucidated the role of SHP2 in the fate determination of mesenchymal stem cells.

Zuo et al., "SHP2 Regulates Skeletal Cell Fate by Modifying SOX9 Expression and 1 Transcriptional Activity." Bone Research 6:12 (2018). The inventors previously elucidated the role of SHP2 in the fate determination of mesenchymal stem cells.

Materials and Methods

Transoenic Mice.

Figure 4:
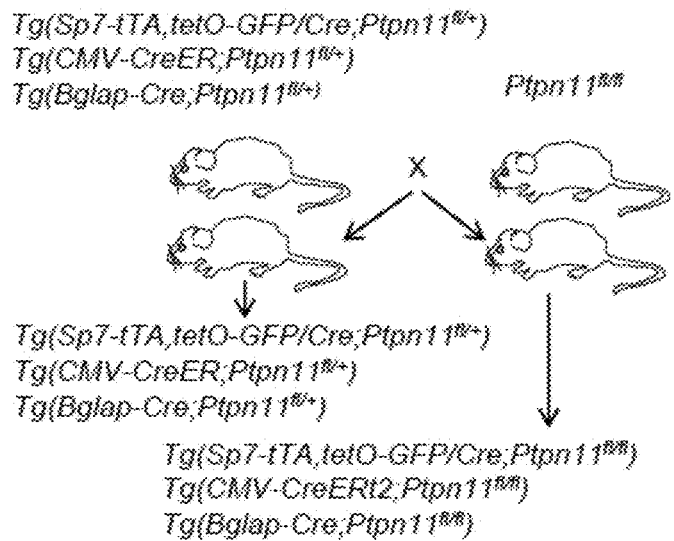
FIG. 4 is a set of drawings. 4(A). This cartoon shows breeding schemes to generate Osterix-expressing cell-specific SHP2 deficient mice and littermate controls. 4(B). This table lists mouse genotypes and shorthand nomenclature. 4(C). This pair of Western blots show reduced expression of SHP2 in calvarial osteoblasts from $SHP2_{sp7}$KO mice compared to $SHP2_{sp7}$CTR mice, and in osteoblasts from $SHP2_{cmv}$KO/ER mice treated without (−) and with (+) tamoxifen (TM) for forty-eight hours. ACTIN serves as internal loading controls.
Figure 4:
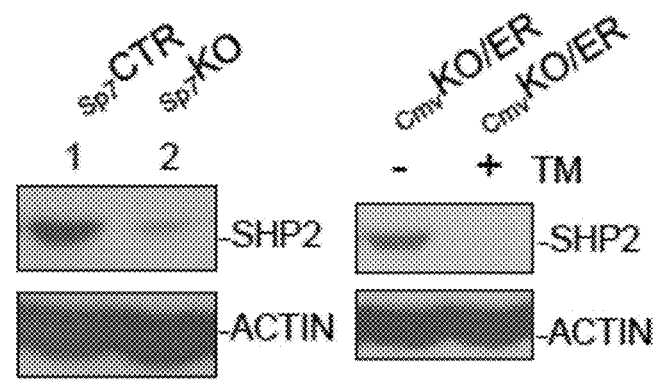

The Ptpn11 floxed (Ptpn11fl), Tg(Rosa26ZsG)17, Tg(Sp7-tTA,tetO-GFP:Cre), and Tg(CMV-CreERt2)33 mice have been described previously. PCR genotyping conditions for these genetically modified mice are described in the original publications by Yang et al., Nature, 499, 491-495 (2013); Madisen et al., "Nature Neuroscience, 13, 133-140 (2010); Rodda & McMahon, Development, 133, 3231-3244 (2006); and Feil et al., Proc. Natl. Acad. Sci. U.S.A., 93, 10887-10890 (1996). To delete Ptpn11 in cells that express the zinc finger-containing transcription factor OSTERIX (Osx or Sp7), or in crypt cells in a tamoxifen-inducible manner, mice bearing a Ptpn11 foxed allele were interbred to Tg(Sp7-tTA,tetO-GFP:Cre) or Tg(CMV-CreERt2) mice to generate offspring with indicated genotypes and nomenclature. See, FIG. 4($a$). To trace Osx-expressing cells in vivo, a Tg(Rosa26$^{ZSG}$) reporter allele was bred to SHP2$_{Sp7}$CTR and SHP2$_{Sp7}$KO mice. All transgenic mice were maintained on a C57BL/6 background and studied according to the Institutional Animal Care and Use Committee approved protocols.

Antibodies and Reagents.

Polyclonal and monoclonal antibodies (PcAb and McAb) were purchased from commercial sources: PcAb against phospho(p)-ERK1/2, ERK1/2, pSTAT3, β-CATENIN, CASPASE3, OLFM4 were from Cell Signaling Inc. (MA). PcAb against CDX2 and OSTERIX and McAb against ACTIN can be purchased from Abcam, Cambridge, Mass. USA. Antibodies against CD45, pSMAD1/5/8, SHP2, and LYSOZYME can be bought from BD Pharmingen, Millipore, Santa Cruz, Calif., USA, and DAKO North America, Carpinteria, Calif., USA. An EdU-labeling and staining kit can be purchased from Life Technologies, ThermoFisher, Carlsbad, Calif., USA. Texas Red-Goat anti-Rabbit IgG was purchased from Invitrogen. Alcian blue staining solution was purchased from Poly Scientific R&D Corp., Bay Shore, N.Y., USA.

Histology, Live-Cell Lineage Tracing, and Immunostaining.

To trace the fate of Osx-expressing cells in the epithelium in mice, small intestines were collected from 4-week-old SHP2$_{Sp7}$CTR:R26$^{ZSG}$ and SHP2$_{Sp7}$KO:R26$^{ZSG}$ mice, fixed in 4% PFA overnight, and embedded in OCT. Frozen sections (7 μm) were used to visualize green fluorescent protein (GFP)-positive cells microscopically. OSTERIX expression in the GFP$^+$ epithelial cells was visualized using anti-OSTERIX immunostaining (1:100). DAPI was used to counterstain the nucleus. Paraffin and frozen sections of small intestines were stained with hematoxylin and eosin (H&E) to visualize general histology and stained with Alcian blue and antibodies against s-CATENIN (1:200), OLFM4 (1:100), CDX2 (1:200), and LYSOZYME (1:200) to evaluate the development, number, and distribution of enterocytes, goblet cells, and Paneth cells in the epithelium. All fluorescent and phase-contrast photographic images were obtained using a Nikon digital fluorescence microscope and an Aperio slide scanner (Vista, Calif., USA). Immunostaining was carried out using either Vectorstain ImmPACT/DAB kits following the manufacturer's instructions or using fluorochrome-labeled secondary antibodies.

Isolation of Intestinal Crypts and Organoid Culture.

Small intestine crypts were isolated from 4-week-old SHP2$_{Sp7}$CTR:R26$^{ZSG}$ and SHP2$_{Sp7}$KO:R26$^{ZSG}$ mice or 8-week-old Tg(Ptpn11$^{fl/fl}$;Cmv-CreER) mice using the method described by Fan et al., Methods Mol. Biol. (2016). Briefly, the inventors harvested small intestines, cleaned them, and cut them into 2-3 mm sections. The cut sections were incubated in PBS with five mM EDTA for 40 minutes on ice with constant stirring. After washing with PBS, detached tissues were collected and passed through a 70 μm filter to obtain pure crypts. Forty μl of matrigel containing 1,000 crypts were seeded in one well of a 48-well plate and cultivated using 400 μl of Small Intestinal Organoid Growth Media as described by O'Rourke et al., Bio. Protoc., 6 (2016). The growth medium was replaced every other day.

Cell Lysate Preparation and Western Blot Analysis.

Cells were lysed in modified NP-40 lysis buffer (0.5% NP40, 150 mM NaCl, 1 mM EDTA, 50 mM Tris [pH 7.4]), supplemented with a protease inhibitor cocktail (1 mM PMSF, 10 mg/ml aprotinin, 0.5 mg/ml antipain, and 0.5 mg/ml pepstatin). Immunoprecipitations were performed on cleared lysates, as described previously by Yang et al., Dev. Cell., 10, 317-327 (2006).

For immunoblotting, cell lysates (30-50 µg) were resolved by SDS-PAGE, transferred to PVDF membranes, and incubated with primary antibodies for two hours or overnight at 4° C. (according to the manufacturer's instructions), followed by HRP-conjugated secondary antibodies, which can be purchased from Bio-Rad, Irvine, Calif., USA.

Patients Specimens and Immuno-Tissue Microarray Analysis.

Seventy-six colon cancer cases were retrieved from the archives of the Department of Pathology, Rhode Island Hospital between 2000 and 2014. Paraffin blocks containing areas of carcinomas were identified on the H&E-stained sections. In each case, areas of the tumor were identified and marked on the source block. The source block was cored, and a 1-mm core was transferred to the recipient "master block" using the Beecher automated tissue arrayer (Beecher Instruments, Silver Spring, Md., USA). Three to six cores of each tumor were arrayed per specimen. A core of normal healthy colon tissue was also sampled. Those having ordinary skill in the biomedical art can perform immunohistochemistry for OSTERIX (1:750) on 4-µm paraffin sections using the DAKO Envision+Dual Link System and the DAKO Liquid 3,3'-Diaminobenzidine Substrate Chromagen System (DAKO North America, Carpinteria, Calif., USA) on each tissue microarray section. Testicle tissue can be used as a positive control. Negative controls were included by the replacement of the primary antibody with nonreactive antibodies of the same species. Immunohistochemical results were evaluated semi-quantitatively, using the method of Jourdan et al., Virchows Arch., 443, 115-121 (2003). Multiple representative sections of colon cancer were examined, as was normal healthy colon tissue from the same patients. The Institutional Review Board at the Rhode Island Hospital approved this study.

Statistical Analysis.

Statistical differences between groups were evaluated using Student's t tests (p values <0.05 were considered to be significant). Analyses were performed by using Prism 6.0 (GraphPad, San Diego, Calif., USA) and Microsoft Excel.

Diagnostic Assay

The invention provides a method for diagnosing gastrointestinal cancer in a subject thereof, comprising the steps of (a) providing a biological sample from the subject; (b) determining the amount in the sample of OSTERIX marker, and (c) comparing the amount of OSTERIX marker in the biological sample to a control amount of OSTERIX marker in a corresponding sample. The subject is diagnosed as having gastrointestinal cancer if there is a measurable increase in the amount of OSTERIX marker in the subject's biological sample as compared to the amount of OSTERIX marker in the control biological sample.

In one embodiment of the diagnostic assay, an increased amount of OSTERIX marker in a biological sample from a subject as compared to the concentration of OSTERIX protein in normal controls is indicative of gastrointestinal cancer.

In another embodiment of the diagnostic assay, an increased concentration of OSTERIX protein in a gastrointestinal sample from a subject as compared to the concentration of OSTERIX protein in normal controls as accepted by those of skill in the oncological art is indicative for gastrointestinal cancer.

EXAMPLE 3 below demonstrates yet another embodiment of the diagnostic assay. Those of ordinary skill in the biomedical art can observe and measure OSTERIX expression in gastrointestinal crypt cells and their descendants. Control and malignant tissue paraffin sections are stained with an anti-OSTERIX antibody. Those of ordinary skill in the biomedical art then evaluate the OSTERIX level in normal gastrointestinal tissues and tumor lesions semi-quantitatively by light microscopy. Immunostaining results are evaluated semi-quantitatively. Cells that display a well-localized and strong staining pattern for OSTERIX are scored as 3+, moderately intense staining as 2+, and weak staining as 1+.

Prognostic Assay

The invention provides a method for determining whether to initiate or continue prophylaxis or treatment of gastrointestinal cancer in a subject, comprising: (a) providing a series of biological samples from the subject over a time period; (b) analyzing the series of biological samples to determine the amount of OSTERIX marker in the subject's biological sample; (c) determining the measurable change in the amount of OSTERIX marker in the biological samples, and (d) determining based upon the measurable change whether to initiate or continue the prophylaxis or therapy of gastrointestinal cancer.

For guidance, see Lamba et al., "Current management and prognostic features for gastrointestinal stromal tumor (GIST)." Exp. Hematol. Oncol. 1, 14 (Jun. 18, 2012); and Yang et al., "Clinicopathological characteristics and prognostic factors of gastrointestinal stromal tumors in Chinese patients." Oncol. Lett., 16(4), 4905-4914 (October 2018). For further guidance, see Ghatalia et al., "Clinical Utilization Pattern of Liquid Biopsies (LB) to Detect Actionable Driver Mutations, Guide Treatment Decisions and Monitor Disease Burden During Treatment of 33 Metastatic Colorectal Cancer (mCRC) Patients (pts) at a Fox Chase Cancer Center GI Oncology Subspecialty Clinic." Front. Oncol. (Jan. 17, 2019).

Method of Treatment

The invention provides a method for selectively treating gastrointestinal cancer in a patient in need thereof, comprising the steps of (a) selecting a patient for treatment with an anticancer agent based on the patient having an increased level of OSTERIX marker as compared to a patient without gastrointestinal cancer; and (b) administering a therapeutically effective amount of an anticancer agent or method to the patient.

Anticancer agents and methods for treating gastrointestinal tumors are known to those having ordinary skill in the oncological arts.

For resectable, primary gastrointestinal tumors, surgery is the most common first step. Those having ordinary skill in the surgical arts can obtain guidance for surgery in the treatment guidelines developed by the National Comprehensive Cancer Network (NCCN) Clinical Practice Guidelines in Oncology (NCCN Guidelines) (United States) and the European Society for Medical Oncology (ESMO) Clinical Practice Guidelines.

Non-drug treatments include Radio Frequency Ablation (RFA) and Hepatic Arterial Chemoembolization (HACE). Radio Frequency Ablation (RFA) is a minimally invasive procedure used to heat and destroy small liver tumors. RFA uses a needle electrode that is inserted through the abdomen wall into tumors in the liver. Those of skill in the surgical art will know the limit to the size and volume of tumors that can be treated with RFA. Hepatic Arterial Chemoembolization (HACE) is a procedure that uses a catheter to deliver chemotherapy directly to the arteries supplying liver tumors. In addition to the chemotherapy, an embolic agent (a device or agent to block the blood vessel) is placed inside the blood vessel, trapping the chemotherapy in the tumor. HACE increases both the dose of chemotherapy that can be delivered to the tumor and decreases the amount of chemotherapy that is delivered to the rest of the body. This chemotherapy is often called chemoembolization. Despite the growing use of targeted drug therapies, HACE remains a treatment approach that can sometimes be used.

Several drugs are commonly used in adjuvant and neo-adjuvant therapy to treat gastrointestinal stromal tumors (GIST). Gleevec (imatinib) is the 'first-line' therapy for the treatment of GIST. Gleevec can be used before surgery to shrink a tumor and after surgery to prevent or delay a recurrence of cancer. Sutent® (sunitinib) and Stivarga® (regorafenib) are the second and third-line therapies, respectively, especially for patients that are resistant or intolerant to Gleevec. Ayvakit® (avapritinib) was approved by the U.S. Food & Drug Administration for treatment in PDGFRA exon 18 mutations. Ayvakit® has been proposed for use as a fourth-line or later GIST treatment.

EGFR inhibitors, including monoclonal antibodies (cetuximab, panitumumab, and necitumumab) and tyrosine kinase inhibitors (erlotinib, geftinib, afatinib, lapatinib, and osimertinib) have been approved for various cancers. The mechanisms of action for EGFR inhibitors include the following properties: (a) interference with cell-cycle progression with arrest in the G1 phase before DNA synthesis; (b) antiangiogenic activity through downregulation of angiogenic factor secretion such as vascular endothelial growth factor (VEGF); (c) inhibition of tumor cell invasion and metastasis by decreasing matrix metalloproteinase production and; (d) promoting apoptosis which enhances the effectiveness of cytotoxic therapy.

Cetuximab is a chimeric monoclonal IgG-1 antibody that was initially approved for treatment in refractory mCRC by the Food and Drug Administration (FDA). Cetuximab was later approved in combination with 5-FU, leucovorin, and irinotecan (FOLFIRI) in the first-line treatment of patients with mCRC. Cetuximab has been administered weekly with a loading dose of 400 mg/m2 intravenously over two hours during the first week, followed by 250 mg/m$^2$ intravenously over one hour weekly. The NCCN guidelines allow for using both the weekly and biweekly schedules of cetuximab.

Panitumumab is a fully-humanized recombinant monoclonal IgG-2 kappa antibody which demonstrated good single-agent activity in EGFR expressing tumors in mouse models and is expected to exhibit minimal immunogenicity and therefore allows for repeated administrations without the development of antibodies. The FDA approved panitumumab as a single agent. Panitumumab was approved as single-agent therapy with dosing of six mg/kg iv every two weeks.

Early-phase clinical trials had suggested a potential benefit in unselected patients with gastroesophageal adenocarcinoma (GEA). Disappointingly, these phase III trials were negative. However, studies using real-world data and other analyses have suggested that EGFR inhibitors and combinations of EGFR inhibitors and other treatments can be therapeutically useful in the treatment of selected gastrointestinal tumors. Haraldsdottir & Bekaii-Saab, "Integrating anti-EGFR therapies in metastatic colorectal cancer." Journal of Gastrointestinal Oncology, 4(3) (September 2013); Maron et al., "Targeted Therapies for Targeted Populations: Anti-EGFR Treatment for EGFR-Amplified Gastroesophageal Adenocarcinoma." Cancer Discov., 8(6), 696-713 (Jun. 1, 2018); Nakamura et al., "HER2-targeted therapy should be shifted towards an earlier line for patients with anti-EGFR-therapy naïve, HER2-amplified metastatic colorectal cancer." ESMO Open; 4, e000530 (2019); Kawakami et al., "587P—The impact of late-line treatment on overall survival (OS) from the initiation of first-line chemotherapy (CT) for patients (pts) with metastatic colorectal cancer (mCRC)." Annals of Oncology, 30(5), page v222 (October 2019).

Active agents, including anti-VEGF and anti-EGFR antibodies, have been used to treat gastrointestinal tumors. Late-line treatment with regorafenib (REGO) or trifluridine/tipiracil (FTD/TPI) has been used.

Immune system cells have proteins that act as checkpoints to keep them from attacking other healthy cells in the body. Newer drugs called immune checkpoint inhibitors work by blocking these checkpoint proteins, which can boost the immune response against cancer cells in the body. These drugs have been shown to be helpful against many types of cancer in recent years. Some of these drugs, such as nivolumab (Opdivo) and ipilimumab (Yervoy), are now being studied for use against gastrointestinal tumors.

The following EXAMPLES illustrate the invention, but should not be considered to limit its scope.

Example 1

SHP2 Deletion in Osterix-Expressing Cells Causes Growth Retardation, Juvenile Lethality, and Gross Gastrointestinal Pathology The inventors discovered OSTERIX expression in the gastrointestinal system during an investigation of SHP2's regulatory role in the bone-forming osteoblasts.

The inventors generated Osterix*-cell-specific SHP2 deficient mice via Osterix (Sp7)-Cre-mediated deletion of the SHP2 encoding gene, Ptpn11. These Osx-expressing, cell-specific, SHP2-knockout mutants developed a modest osteopenic phenotype.

Unexpectedly, the SHP2 mutants failed to thrive. SHP2 deletion in Osx-expressing cells in mice led to dwarfism, gastrointestinal dysplasia, and juvenile lethality. The inventors observed and produced photographic images of 4-week-old male mice that showed marked growth retardation in $SHP2_{Sp7}KO$ mice, as compared with $SHP2_{Sp7}CTR$ mice. The SHP2 knockout mutants died within six weeks of birth. See the Kaplan-Meier curve in FIG. 1.

Necropsies of the mutants revealed gross intestinal pathology. Microscopic analysis of paraffin and frozen sections revealed marked reductions in the number and length of villi of the small intestines. These data showed that the Osterix promoter was active in the cells of the gastrointestinal epithelium.

The inventors produced a pair of photographic images from necropsies of 4-week-old mice. The photographic images showed gaseous bloating and multiple "balloon-shape" lesions on small and large intestines of $SHP2_{Sp7}KO$, but not $SHP2_{Sp7}CTR$ control mice (n=8). The inventors produced another pair of photographic images from necropsies of 4-week-old mice. The photographic images showed gaseous bloating and multiple "balloon-shape" lesions on small and large intestines of $SHP2_{Sp7}KO$ mice, but not on the intestines of $SHP2_{Sp7}CTR$ control mice (n=8).

Example 2

Osterix Promoter is Active, and OSTERIX Protein is Expressed in Gastrointestinal Crypt Cells The inventors directly examined the expression of OSTERIX in cells of the gastrointestinal epithelium. Immunostaining of frozen sections of the small intestine revealed robust expression of OSTERIX in non-Paneth cells in the crypts, along with reduced expression in the villi.

The inventors produced a pair of fluorescent images of ileum frozen sections from 4-week-old Tg(Sp7-Cre: R26ZSG) mice, without and with DAPI counterstain (n=6). Green fluorescence identifies cells in which the Osterix promoter is or has been active. The inventors also produced a pair of photographic images showing the immunostaining of ileum frozen sections from 4-week-old Tg(Sp7-Cre; R26ZSG) mice with anti-OSTERIX antibodies, with and without DAPI counterstain (n=4). Yellow fluorescence reflected cells in which OSTERIX was expressed and in which Osterix promoter is or has been active.

Example 3

OSTERIX is a Marker for Gastrointestinal Stem Cells

The immunostaining findings in EXAMPLE 2 were strengthened by the cell lineage tracing studies in this EXAMPLE, in which Tg(Sp7-Cre) mice were crossed to Rosa26ZSG reporter mice. The purpose of this EXAMPLE is to show that increased OSTERIX expression is correlated with neoplastic lesions in humans.

The inventors produced a pair of phase-contrast photographic images of the crypt organoid cultures at the 36-hour time point, without (i) and with (ii) fluorescent overlay (n=12). These photographic images showed green fluorescent protein (GFP) in the original and budding crypt cells. These images thus showed that the Osterix promoter is active in dividing crypt cells. The inventors also produced a pair of fluorescent images of the small intestine crypt stained with antibodies against OSTERIX and OLFM4. These photographic images showed the existence of OSTERIX$^+$ cells in the crypt. These images thus showed that these cells colocalized with OLFM4 expression in the crypt.

Characterization of Tg(Sp7-Cre:Rosa26ZsG) compound mice revealed OSTERIX promoter-driven green fluorescent protein expression throughout the crypts and villi of the gastrointestinal epithelium. These data showed that the Osx promoter is active in the gastrointestinal crypt cells and that that OSTERIX is expressed in gastrointestinal stem cells.

The inventors observed and measured OSTERIX expression in gastrointestinal crypt cells and their descendants. The inventors produced photographic images of anti-OSTERIX-stained normal and carcinomatous tissues. These images show the increased expression of OSTERIX with malignancy. Control and malignant tissue paraffin sections (4 μm) were stained with an anti-OSTERIX antibody using the DAKO Envision+Dual Unk System.

The inventors then evaluated the OSTERIX level in normal gastrointestinal tissues and tumor lesions semi-quantitatively by light microscopy. Seventy-six colon cancer cases and forty-four controls were retrieved from the archives of the Department of Pathology, Rhode Island Hospital of cases diagnosed between 2000 and 2014. Immunostaining results were evaluated semi-quantitatively. Cells that displayed a well-localized and strong staining pattern for OSTERIX were scored as 3+, moderately intense staining as 2+, and weak staining as 1+. *p<0.05, X2 test. Cells that displayed a well-localized and strong staining pattern for SP7 were scored as 3+, moderately intense staining as 2+, and weak staining as 1+. The extent of staining (percentage of cells staining) was 100% in each case. At least three cores were scored per case because another study has shown that the analysis of three cores per case is comparable with the analysis of the whole section.

OSTERIX expressed at a very low level in the normal gastrointestinal epithelium. However, the expression increased markedly in ~60% of the gastrointestinal tumors.

TABLE 1

| Grade | 0 | +1 | +2 | +3 |
| --- | --- | --- | --- | --- |
| Normal | 10 | 25 | 9* | 0 |
| Colon adenocarcinoma | 0 | 6 | 38* | 32* |

These data show that OSTERIX is a marker for gastrointestinal stem cells. As such, OSTERIX is a diagnostic and prognostic marker of gastrointestinal tract tumors.

Example 4

Human Tumor Tissue Screening Confirms the Usefulness of OSTERIX as a Tumor Marker, OSTERIX is Expressed at a Low Level in the Normal Gastrointestinal Epithelium, and its Level Markedly Increases in Benign and Malignant Gastrointestinal Tumor Tissue.

To explore the clinical significance and usefulness of OSTERIX in the gastrointestinal epithelium, the inventors conducted tissue array analysis to determine the profile of OSTERIX expression in healthy, benign, and malignant human gastrointestinal tissues. Thirty-six colon cancer cases were retrieved from the archives of the Department of Pathology, Rhode Island Hospital between 2000 and 2014. Several representative sections of colon cancer were examined. Normal colon from the same patient was also observed in each case. The Institutional Review Board at the Rhode Island Hospital approved this screening (RIH Protocol IRB #000799).

The inventors performed immunohistochemistry OSTERIX assays on 4-μm paraffin sections of each colon tissue microarray section described above. Slides were stained with anti-OSTERIX (1:750; ab22552 Abcam) using the DAKO Envision+Dual Link System and the DAKO Liquid 3,3'-Diaminobenzidine Substrate Chromagen System (DAKO North America, Carpinteria, Calif., USA). Testicle tissue was a positive control. Negative controls included the replacement of the primary antibody with nonreactive antibodies of the same species.

The inventors performed an immunostained tissue array analysis that demonstrates the expression profile of OSTERIX in healthy (28) and malignant (38) gastrointestinal tissues. In anti-OSTERIX-immunostained malignant gastrointestinal tissue, OSTERIX was diffusely expressed and markedly elevated, as compared with anti-OSTERIX-immunostained healthy control tissue.

Example 5

SHP2 Regulates the Gastrointestinal Epithelium by Modifying OSTERIX$^+$ Crypt Stem Cells The purpose of this EXAMPLE was to study further the function of the protein tyrosine phosphatase SHP2 in mouse skeletal development.

The inventors generated mice in which Ptpn11 was inactivated in their Osterix-expressing preosteoblasts by crossing Tg(Sp7-Cre) and Ptpn11$^{fl/+}$ mice. Rodda & McMahon, Development, 133, 3231-3244 (2006). Yang et al., Nature, 499, 491-495 (2013). Yang et al., Dev. Cell., 10, 317-327 (2006). See also, FIG. 4(a)-(b). In some mice, Tg(Rosa26ZSG) was bred-in as a reporter of Cre expression. Madisen et al., Nature Neuroscience, 13, 133-140 (2010). In other mice, Cre activity was made inducible by tamoxifen, and its expression was driven by the chicken beta-actin promoter/enhancer coupled with the cytomegalovirus (CMV) immediate-early enhancer (Cmv-CreER). Maes et al., Dev. Cell 19, 329-344 (2010).

Previous studies of SHP2 deletion in mouse epithelium via 12.4 kb villin-Cre-mediated Ptpn11 excision had resulted in chronic colitis with an inflammatory cell infiltration, increased STAT3 activation, and decreased ERK1/2 phosphorylation. See, Coulombe at al., Mol. Cell. Biol. 33, 2275-2284 (2013); Heuberger et al., Proc. Natl. Acad. Sci. U.S.A., 111, 3472-3477 (2014); Yamashita et al., PloS one 9, e92904 (2014).

Figure 5:
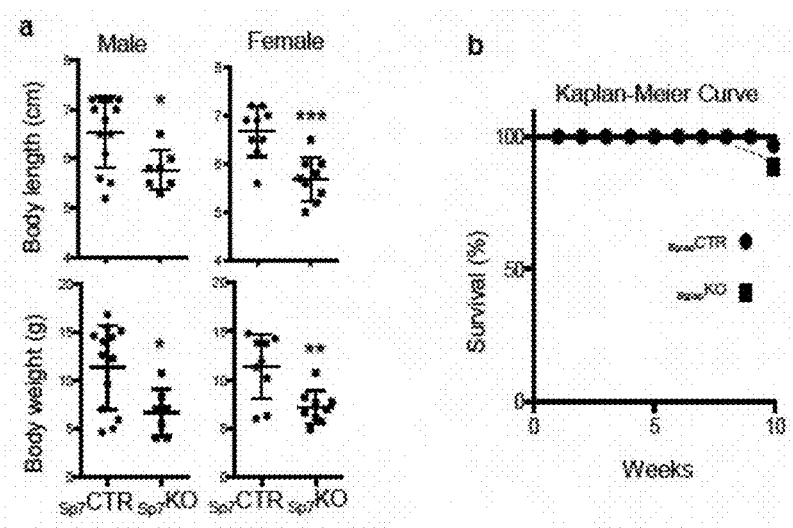
FIG. 5 is a set of graphs showing that mice lacking SHP2 in the Osterix+ have decreased body weight and length. (a) The bar graphs show the body weight and length of 4-week-old $SHP2_{Sp7}$CTR and $SHP2_{Sp7}$KO mice (Student's t test, *$p<0.05$, $p<0.01$, *$p<0.001$). (b) The Kaplan-Meier survival curves of $SHP2_{Bglap}$CTR and $SHP2_{Bglap}$KO mice at the age of week ten (n=19/per genotype).

In this EXAMPLE, the Tg(Sp7-Cre:Ptpn11$^{fl/fl}$) (SHP2$_{Sp7}$ KO) mice were born at the expected Mendelian ratio and appeared healthy at birth. Their subsequent growth was dramatically retarded as compared to the Tg(Sp7-Cre:Ptpn11$^{fl/+}$) littermate controls (SHP2$_{Sp7}$CTR). At four weeks of age, the lengths and weights of the SHP2$_{Sp7}$KO mice were only ~65% and ~51% of the SHP2$_{Sp7}$CTR mice, respectively. Compare, FIG. 5 and results in EXAMPLE 1, above. The SHP2$_{Sp7}$ KO mice were mildly osteoporotic, which was consistent with the targeting of SHP2 in preosteoblasts. Unexpectedly (see also, EXAMPLE 1), the SHP2$_{Sp7}$KO pups began to die starting at two weeks of age. None survived beyond week six.

By contrast, contemporaneously bred mice with SHP2 inactivated in mature osteoblasts via Bglap-Cre (i.e., the SHP2$_{Bglap}$KO mutants) were viable and healthy through ten weeks of age. See, FIG. 5(b). This genetic result showed that the juvenile lethality of SHP2$_{Sp7}$KO mice was not due to SHP2-related osteoblast dysfunction.

The inventors performed necropsies on the SHP2$_{Sp7}$KO mice. The necropsies revealed gross gaseous distension and hemorrhage along the length of the small and large intestines consistent with primary gastrointestinal pathology. Necropsy photographic images from 4-week-old SHP2$_{Sp7}$KO mice showed bloated tracts and hemorrhage in the small and large intestines. SHP2$_{Sp7}$CTR animals served as controls.

Figure 2:
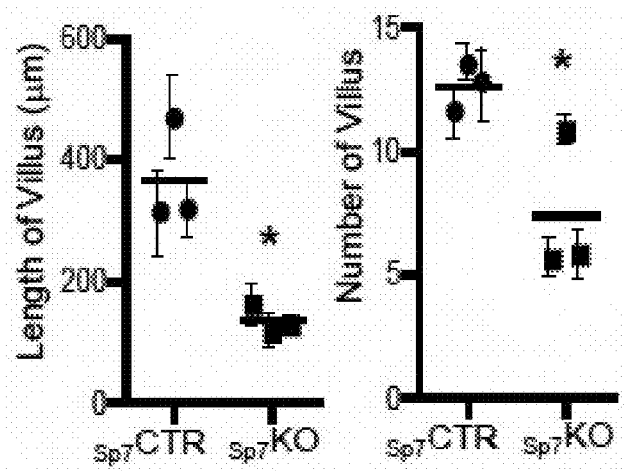
FIG. 2 is a pair of graphs showing the quantitative data for the height and number of villi corresponding to photographic images of H&E-stained ileal paraffin sections generated by the inventors. The photographic images showed villus hypoplasia in 4-week-old $SHP2_{Sp7}$CTR and $SHP2_{Sp7}$KO mice (means t SD; ***$p<0.001$, Student's t test; n=5).

The inventors performed a histopathological examination of gut samples from the mice in this EXAMPLE. The histological studies revealed dramatically truncated villi in the ileum. Photographic images of H&E-stained ileal paraffin sections showed villus hypoplasia in 4-week-old SHP2$_{Sp7}$CTR and SHP2$_{Sp7}$KO mice. The quantitative data for the height and number of villi are shown in FIG. 2.

SHP2 deletion in Osx-expressing cells in mice led to dwarfism, dysplasia, and juvenile lethality. The inventors produced representative photographic images of age-matched and sex-matched 4-week-old mice. These images showed the skeletal dwarfism in the SHP2$_{Sp7}$KO mice compared with the SHP2$_{Sp7}$CTR at four weeks of age.

These histological examinations revealed no apparent evidence of inflammatory infiltrate or cell apoptosis. The inventors confirmed the lack of inflammation and cell death by immunostaining for STAT3, ERK1/2, CASPASE 3, and CD45. The immunostaining revealed no discernible differences between the SHP2$_{Sp7}$KO and SHP2$_{Sp7}$CTR mice.

Mice Lacking SHP2 in Osx$^+$ Cells Displayed Villus Hypodysplasia.

The inventors produced photographic images that showed H&E stained "Swiss roll" paraffin sections (n=4) displayed the gross histology of small and large intestines of the 4-week-old SHP2$_{Sp7}$CTR and SHP2$_{Sp7}$KO mice. Fluorescent photographic images of immunostained ileal frozen sections showed comparable activation of ERK1/2 (Thr$_{202}$/Tyr$_{204}$), STAT3 (Tyr$_{705}$), and the expression of active CASPASE3 in the villi and crypts of SHP2$_{Sp7}$CTR mice and SHP2$_{Sp7}$KO mice. Fluorescent images of ileum frozen sections stained with anti-CD45 antibodies (n=3) showed the infiltration of inflammatory cells.

This immunostaining result showed that the Osterix-Cre-driven SHP2 knockout phenotype was distinct from the Villin-Cre phenotype. See, Coulombe et al., Mol. Cell. Biol. 33, 2275-2284 (2013); Heuberger et al., Proc. Natl. Acad. Sci. U.S.A., 111, 3472-3477 (2014); and Yamashita at al., PloS one 9, e92904 (2014).

The Osterix (Osx/Sp7) Promoter is Active, and OSTERIX is Expressed in Crypt Cells.

The inventors examined ileum samples by fluorescent microscopy. The fluorescent photographic images of ileum frozen sections demonstrate the existence of R26ZSG$^+$ cells in the villi and crypts of 4-week-old Sp7-Cre:R26ZSG mice. The inventors saw a strong cellular expression of the Rosa26ZSG reporter in both the intestinal crypts and villi of 4-week-old SHP2$_{Sp7}$CTR mice, indicating that the Osterix promoter was or had been active in stem cells and differentiated enterocytes. Confirmatory immunostaining with an antibody against murine OSTERIX localized only to the base of the crypts. The cells at the base of the intestinal crypts are intestinal stem cells and Paneth cells, with an occasional label-retaining cell. Barker et al., Nature, 449, 1003-1007 (2007); Barker et al., Cell Stem Cell, 11, 452-460 (2012); Clevers, Cell, 154, 274-284 (2013); and Clevers & Batlle, Cell, 152, 1198-1198 e1192 (2013). The fluorescent images of anti-OSTERIX antibody-stained ileal frozen sections demonstrated the coiocalization of OSTERIX and R26$^{ZSG}$ reporter in the crypt cells.

The Osterix (Osx/Sp7) Promoter is Active, and OSTERIX is Expressed in Gastrointestinal Crypt Cells.

The inventors then performed another round of ileal immunostaining using primary antibodies against the stem cell marker OLFM424 and LYSOZYME, an antimicrobial peptide secreted by Paneth cells. Osterix expression co-localized with many of the OLFM4$^+$ cells within the crypts, and not with the I LYSOZYME$^+$ Paneth cells. See van der Filer et al., Gastroenterology, 137, 15-17 (2009); Sato et al., Nature, 469, 415-418 (2011).

The inventors produced photographic images of frozen ileal sections of 4-week-old Sp7-Cre:R26$^{ZSG}$ mice immunostained with anti-OLFM4 and anti-LYSOZYME antibodies, demonstrating the colocalization of OLFM4 or LYSOZYME with R26$_{ZSG}$ reporter in the crypts. Merged phase-contrast and fluorescent images showed the existence of R26$^{ZSG+}$ cells interspersed by the R26$^{ZSG}$ cells at the crypt base in organoid culture. The pictures of human colon paraffin sections stained with ant-OSTERIX antibody demonstrate the existence of OSTERIX$^+$ cells in the crypts.

These results show that the Osterix promoter is active and that OSTERIX protein is expressed in the crypt base columnar stem cells. The results in this EXAMPLE provide direct evidence of Osterix expression during crypt cell self-renewal. The inventors created crypt organoid cultures from SHP2$_{Sp7}$CTR:R26$^{ZSG}$ mice. See, Sato et al. Nature, 469, 415-418 (2011); and Fan et al., Methods Mol. Biol. (2016). The crypt organoid cultures exhibited robust green fluorescent protein (GFP) expression in newly-formed crypt buds, as well as in the initially-isolated crypts. The inventors confirmed cross-species conservation of OSTERIX expression was confirmed by immunostaining healthy human colon tissue.

The inventors next studied the function of SHP2 in the mouse model. The villus hypoplasia was striking. See, FIG. 2.

The inventors first explored the effect of Osterix-driven SHP2 deletion on crypt cell proliferation. The inventors administered EdU to four-week-old mice for two hours. Then, the animals were euthanized. Their small intestines were harvested. Staining of frozen ileum sections revealed significantly fewer EdU-positive cells in the crypts of $SHP2_{Sp7}KO:R26^{ZSG}$ mice compared to the $SHP2_{Sp7}CTR:R26^{ZSG}$ controls.

SHP2 Deletion in Osterix+ Cells Compromises Cell Proliferation but does not Alter the Fate of Goblet Cell, Paneth Cell, and Enterocytes.

Figure 6:
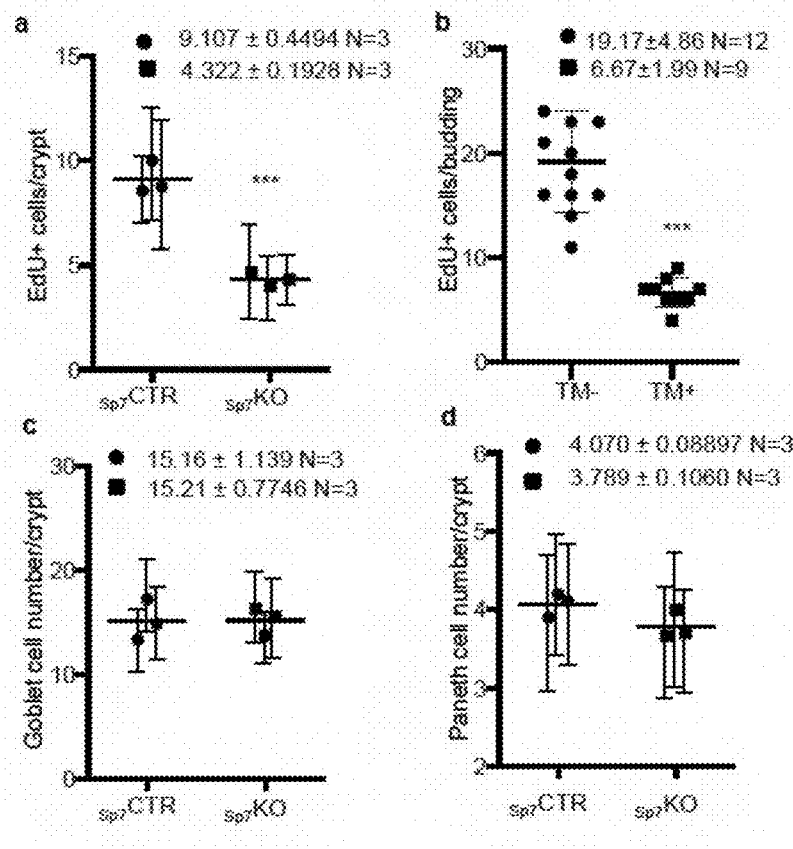
FIG. 6 is a set of graphs showing that the SHP2 deletion in Osterix+ cells significantly compromises the proliferation of crypt CBCs but has minimal effect on the fate and growth of goblet and Paneth cells. (a) The bar graphs demonstrating significantly reduced EdU+ cells per crypt in $SHP2_{Sp7}$KO mice. Fifteen crypts were counted for each mouse. The results of $SHP2_{Sp7}$CTR vs. $SHP2_{Sp7}$KO are 9.10±0.45 vs. 4.32±0.19. (Student's ttest, *$p<0.001$). (b) The bar graphs demonstrated significantly reduced EdU+ cells per bud in crypt organoid culture. The results of $SHP2_{cmv}$KO/TM− vs. $SHP2_{cmv}$KO/TM+ are 19.19±4.86 vs. 6.67±1.99. (Student's ttest, *$p<0.001$). (c)-(d) The bar graphs demonstrated comparable numbers of goblet and Paneth cells in the villi of SHP2Sp7CTR and $SHP2_{Sp7}$KO mice. Fifteen villi/crypts were counted for each mouse. The goblet cell results for SHP2Sp7CTR vs. $SHP2_{Sp7}$KO are 15.16±1.14 vs. 15.21±0.77. The Paneth cell results SHP2Sp7CTR vs. $SHP2_{Sp7}$KO are 4.07±0.09 vs. 3.79±0.11; $p>0.05$.

The inventors produced photographic images of frozen ileal sections, and crypt organoid cultures demonstrated cells positive for EdU+ labeling in the developed and budding crypts. EdU was administered two hours before harvesting the mice and one hour before harvesting the organoid culture cells. The inventors also produced photographic images of ileum frozen sections stained with anti-β-CATENIN and CDX2 antibodies and with Alcian blue. The pictures show the distribution of enterocytes and goblet cells in the vili of 4-week-old mice with indicated genotype. Quantitative data are provided in FIG. 6.

The inventors produced photographic images of crypt organoid culture stained with anti-LYSOZYME antibody demonstrate the formation of Paneth cells in the budding crypts. Crypt organoids were cultured without tamoxifen for four days, and then with vehicle or tamoxifen for two days, EdU was administered two hours before harvesting. The quantitative data were presented as means±SD (n=9, ***p<0.001, Student's t test).

This finding was corroborated using crypt organoid cultures from $SHP2_{Cmv}Cre/ER$ mice, in which SHP2 expression could be controlled by tamoxifen treatment. Crypt budding, growth, and EdU-labeling were robust in the control cultures but severely impaired in the cultures with tamoxifen added to the media.

EdU-labeling in the crypts was reduced in $SHP2_{Sp7}KO$ mice, as was EdU-labeling and budding in crypt organoid cultures from $SHP2_{Cmv}Cre/ER$ mice upon tamoxifen treatment. However, knockdown of SHP2 did not influence the relative numbers of enterocytes, goblet cells, or Paneth cells. Given its function as a master regulator of osteoblast differentiation, OSTERIX may be a significant factor in gut homeostasis, analogous to SOX9's dual role as a master regulator of cartilage formation, and an important regulator of crypt reserve cell biology. Bi et al., "Sox9 is required for cartilage formation." Nature Genetics, 22, 85-89 (1999); Roche et al., "Gastroenterology, 149, 1553-1563 e1510 (2015).

The inventors next sought to determine whether epithelial differentiation was affected by Osterix-Cre SHP2 deletion. The inventors used immunohistochemical and histochemical staining to compare the numbers of enterocytes, goblet cells, and Paneth cells in the small intestine and crypt organoid cultures from $SHP2_{Sp7}CTR:R26^{ZSG}$ and $SHP2_{Sp7}KO:R26^{ZSG}$ mice. βCATENIN, CDX2, and Alcian blue staining revealed similarly-dense populations of normal-appearing enterocytes and goblet cells in both strains of mice, despite the distorted morphology of the villi in the $SHP2_{Sp7}KO:R26^{ZSG}$ animals. Lysozyme staining was comparable in the buds of organoids grown from $SHP2_{Sp7}CTR:R26^{ZSG}$ and $SHP2_{Sp7}KO:R26^{ZSG}$ mice, and from $SHP2_{Cmv}KO:R26^{ZSG}$ mice, with and without tamoxifen treatment.

Collectively, the results in this EXAMPLE show that SHP2 is essential for the self-renewal and proliferation of Osterix+ stem cells and progenitors, but that it has minimal impact on their differentiation.

The inventors next studied the potential molecular mechanisms whereby SHP2 might modulate Osterix+ stem and progenitor cells. Bone morphogenetic proteins (BMPs) are known in the art to induce Osterix expression and osteogenic differentiation of skeletal progenitors. Ulsamer at al., J. Biol. Chem., 283, 3816-3826 (2008); and Salazar et al., Nat. Rev. Endocrinol. 12, 203-221 (2016). Also, BMP4 is expressed by mesenchymal cells adjacent to the crypt, where it down-regulates the self-renewal and proliferation of the crypt stem cells. Qi et al., Nature Communications, 8, 13824 (2017); and He et al., Nature Genetics, 36, 1117-1121 (2004).

Based on this, the inventors studied whether SHP2 might regulate BMP signaling in crypt cells. The inventors isolated crypt cells from 8-week-old $Tg(Cmv-CreER;Ptpn11^{fl/fl})$ mice, thus circumventing the difficulty of culturing crypt cells from $SHP2_{Sp7}KO$ mutants. Fan et al., Methods Mol. Biol. (2016). The cells were cultured in vitro for three days under the condition described previously in O'Rourke et al., "Isolation, Culture, and Maintenance of Mouse Intestinal Stem Cells." Bio. Protoc., 6 (2016). The cells were then treated with tamoxifen (TM) or vehicle for forty-eight hours. The cells were starved, stimulated with BMP4, and then lysed for western blot analysis.

Figure 3:
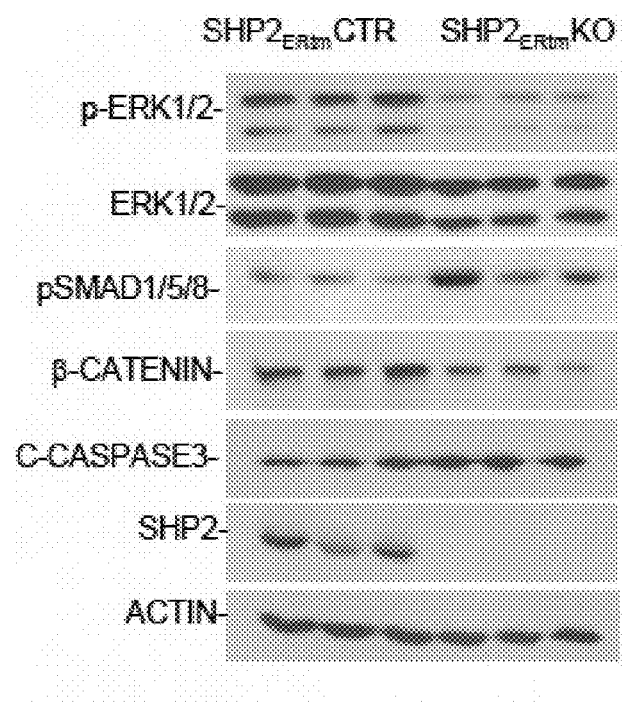
FIG. 3 is a photographic image of several Western blots. SHP2 deletion in Osterix cells compromises cell proliferation but does not alter the fate of goblet cell, Paneth cell, and enterocytes. The Western blots demonstrate defective ERK but enhanced SMAD activation in crypt cells isolated from Tg(Cmv-CreER:Ptpn11fl/fl) mice and treated with tamoxifen (TM). Vehicle treated cells served as controls. Isolated crypts were cultured in vitro for three days and then treated with vehicle or tamoxifen for forty-eight hours. After starvation, they were stimulated with BMP4 and lysed for western blot analysis.

The inventors produced Western blots demonstrating defective ERK but enhanced SMAD activation in crypt cells isolated from $Tg(Cmv-CreER;Ptpn11^{fl/fl})$ mice and treated with tamoxifen (TM). See, FIG. 3. Vehicle treated cells served as controls. Isolated crypts were cultured in vitro for three days and then treated with vehicle or tamoxifen for forty-eight hours.

Tamoxifen treatment resulted in a robust deletion of SHP2, which was associated with compromised ERK and enhanced $SMAD^{1/5/8}$ activation, based on the phosphorylation of their respective activation sites, and reduced β-CATENIN level, but no apparent effect on CASPASE3 cleavage. These data show that BMP4-evoked signaling in crypt stem cells requires SHP2, which may contribute to the phenotype of the $SHP2_{Sp7}KO$ mutants. The inventors' finding of robust OSTERIX expression in the crypt cells and the findings that OSTERIX is overexpressed in certain cancers prompted the inventors to study the translational potential OSTERIX expression in normal and neoplastic tissues. Tissues from seventy-six colon cancer cases diagnosed between 2000 and 2014 were retrieved from the archives of the Department of Pathology at Rhode Island Hospital. The inventors first identified the areas of carcinoma on hematoxylin and eosin-stained sections from paraffin blocks. The inventors then immunostained multiple sections (4 μm) of the tumor and adjacent healthy colon tissue from the same patient with antibodies against human OSTERIX, per an IRB-approved protocol. Immunohistochemical results were evaluated semi-quantitatively. Cells that displayed a well-localized and strong staining pattern for OSTERIX were scored as 3+, moderately intense staining as 2+, and weak staining as 1+. The extent of staining (percentage of cells staining) was 100% in each case. Of the 76 malignant colon adenocarcinoma samples, 70 (92.1%) exhibited strong (>2+) OSTERIX signaling. By contrast, only 9 of 44 (20.4%) samples of normal tissue were OSTERIX positive (>2+), and none scored 3+. See EXAMPLE 3, above. These data confirm that OSTERIX is expressed in the normal human epithelium, and that expression is substantially increased in colonic adenocarcinoma cells. Thus, OSTERIX is a marker for the diagnosis and prognosis of malignancy.

Other Embodiments

Specific compositions and methods have been described. The detailed description in this specification is illustrative and not restrictive. The detailed description in this specification is not intended to be exhaustive or to limit the disclosure to the precise form disclosed. Other equivalents and modifications besides those already described are possible without departing from the inventive concepts described in this specification, as those having ordinary skill in the biomedical art recognize. While method steps or functions are presented in a given order, alternative embodiments may perform functions in a different order, or functions may be performed substantially concurrently. Due to biological functional equivalency considerations, some changes can be made in the protein structure without affecting the biological or chemical action in kind or amount. The inventive subject matter is not to be restricted except in the spirit of the disclosure.

When interpreting the disclosure, all terms should be interpreted in the broadest possible manner consistent with the context. Unless otherwise defined, all technical and scientific terms used in this specification have the same meaning as commonly understood by those having ordinary skill in the art to which this invention belongs. This invention is not limited to the particular methodology, protocols, or reagents described in this specification and can vary in practice. The terminology used in this specification is not intended to limit the scope of the invention, which is defined solely by the claims.

All patents and publications cited throughout this specification are expressly incorporated by reference to disclose and describe the materials and methods described in such publications that might be used with the technologies described in this specification. The publications discussed are provided solely for their disclosure before the filing date. They should not be construed as an admission that the inventors are not entitled to antedate such disclosure by prior invention or for any other reason. If there is an apparent discrepancy between a previous patent or publication and the description provided in this specification, the present specification (including any definitions) and claims shall control. All statements as to the date or representation as to the contents of these documents are based on the information available to the applicants and constitute no admission as to the correctness of the dates or contents of these documents. The dates of publication provided in this specification may differ from the actual publication dates. If there is an apparent discrepancy between a publication date provided in this specification and the actual publication date supplied by the publisher, the actual publication date shall control.

The terms "comprises" and "comprising" should be interpreted as referring to elements, components, or steps in a non-exclusive manner, indicating that the referenced elements, components, or steps may be present, used, or combined with other elements, components, or steps. The singular terms "a," "an," and "the" include plural referents unless context clearly indicates otherwise. Similarly, the word "or" is intended to include "and" unless the context clearly indicates otherwise. The abbreviation "e.g." is used to indicate a non-limiting example and is synonymous with the term "for example."

When a range of values is provided, each intervening value, to the tenth of the unit of the lower limit, unless the context dictates otherwise, between the upper and lower limit of that range and any other stated or intervening value in that range of values.

Some embodiments of the technology described can be defined according to the following numbered paragraphs:

The use of an anticancer agent in the treatment of gastrointestinal cancer in a patient, the treatment comprising: (a) assaying a biological sample from the patient, (b) determining if a patient has an increased level of OSTERIX marker as compared to a biological sample from a patient without gastrointestinal cancer, and (c) if an increased level of OSTERIX marker is present, administering a therapeutically effective amount of the anticancer agent to the patient.

The use of an OSTERIX marker in the assessment of gastrointestinal cancer, wherein an increased amount of OSTERIX marker in a biological sample from a subject as compared to normal controls is indicative of gastrointestinal cancer.

The use of an antibody directed against OSTERIX protein in the assessment of gastrointestinal cancer, wherein an increased concentration of OSTERIX protein in a gastrointestinal sample from a subject as compared to normal controls is indicative for gastrointestinal cancer.

The use of an OSTERIX marker in the assessment of gastrointestinal cancer, wherein the amount of OSTERIX marker in a biological sample is measured using an anti-OSTERIX antibody.

A method for selectively treating gastrointestinal cancer in a patient in need thereof, comprising the steps of (a) selecting a patient for treatment with an anticancer agent based on the patient having an increased level of OSTERIX marker as compared to a patient without gastrointestinal cancer; and (b) administering a therapeutically effective amount of an anticancer agent or method to the patient.

The method for selectively treating gastrointestinal cancer in a patient, wherein the treatment is Radio Frequency Ablation (RFA) or Hepatic Arterial Chemoembolization (HACE).

The method for selectively treating gastrointestinal cancer in a patient, wherein the treatment is selected from the group consisting of imatinib, sunitinib, regorafenib, and avapritinib.

The method for selectively treating gastrointestinal cancer in a patient, wherein the treatment is selected from the group consisting of cetuximab, panitumumab, and necitumumab The method for selectively treating gastrointestinal cancer in a patient, wherein the treatment is selected from the group consisting of erlotinib, gefitinib, afatinib, lapatinib, and osimertinib.

The method for selectively treating gastrointestinal cancer in a patient, wherein the treatment is selected from one or more of anti-EGFR-therapy, anti-VEGF-therapy, HER2-targeted therapy, anti-checkpoint inhibitor proteins, or a combination thereof.

The method for selectively treating gastrointestinal cancer in a patient, wherein the treatment includes regorafenib (REGO) or trifluridine/tipiracil (FTD/TPI).

A method for diagnosing gastrointestinal cancer in a subject thereof, comprising the steps of (a) providing a biological sample from the subject; (b) determining the amount in the sample of OSTERIX marker; and (c) comparing the amount of OSTERIX marker in the biological sample to a control amount of OSTERIX marker in a corresponding sample, wherein the subject is diagnosed as having gastrointestinal cancer if there is a measurable increase in the amount of OSTERIX marker in the subject's biological sample as compared to the amount of OSTERIX marker in the control biological sample.

A method for determining whether to initiate or continue prophylaxis or treatment of gastrointestinal cancer in a subject, comprising: (a) providing a series of biological samples from the subject over a time period; (b) analyzing the series of biological samples to determine the amount of OSTERIX marker in the subject's biological sample; (c) determining the measurable change in the amount of OSTERIX marker in the biological samples, and (d) determining based upon the measurable change whether to initiate or continue the prophylaxis or therapy of gastrointestinal cancer.

A method for identifying gastrointestinal stem cells in a gastrointestinal sample, comprising: (a) providing a gastrointestinal sample; (b) analyzing the gastrointestinal sample to determine the amount of OSTERIX marker; (c) identifying gastrointestinal stem cells in a gastrointestinal sample by the expression of OSTERIX marker in the cells in the gastrointestinal sample.

The invention claimed is:

1. A method for selectively treating gastrointestinal cancer in a patient in need thereof, comprising the steps of:
   (a) selecting a patient for treatment with an anticancer agent;
   (b) providing a series of biological samples from the subject over a time period;
   (c) analyzing the series of biological samples to determine the amount of OSTERIX marker in the subject's biological samples;
   (d) determining the change in the amount of OSTERIX marker in the biological samples; and
   (e) determining based upon the change whether to initiate or continue the prophylaxis or therapy of gastrointestinal cancer, and
   (f) administering a therapeutically effective amount of an anticancer agent or method to the patient,
   wherein the anticancer agent or method is selected from the group consisting of:
      (i) non-drug treatments selected from the group consisting of Radio Frequency Ablation (RFA) and Hepatic Arterial Chemoembolization (HACE);
      (ii) adjuvant or neoadjuvant therapy selected from the group consisting of imatinib, sunitinib, regorafenib, and avapritinib;
      (iii) EGFR inhibitors selected from the group consisting of cetuximab, panitumumab, and necitumumab;
      (iv) tyrosine kinase inhibitors selected from the group consisting of erlotinib, geftinib, afatinib, lapatinib, and osimertinib;
      (v) cetuximab, either alone or combination with 5-FU, leucovorin, and irinotecan;
      (vi) panitumumab;
      (vii) regorafenib;
      (viii) trifluridine/tipiracil; and
      (ix) immune checkpoint inhibitors selected from the group consisting of nivolumab and ipilimumab.

2. The method of claim 1, wherein the selecting a patient for treatment with an anticancer agent comprises identifying gastrointestinal stem cells in a gastrointestinal sample.

3. The method of claim 1, wherein the selecting a patient for treatment with an anticancer agent comprises identifying gastrointestinal stem cells in a gastrointestinal sample and analyzing the gastrointestinal sample to determine the amount of OSTERIX marker.

4. The method of claim 1, wherein the selecting a patient for treatment with an anticancer agent comprises identifying gastrointestinal stem cells in a gastrointestinal sample by the expression of the OSTERIX marker in the cells in the gastrointestinal sample.

5. The method of claim 1, wherein the method for selectively treating gastrointestinal cancer in a patient further comprises the step of:
   (g) determining whether to continue prophylaxis or treatment of gastrointestinal cancer in the subject.

* * * * *